(12) United States Patent
Khanna

(10) Patent No.: US 9,480,503 B2
(45) Date of Patent: Nov. 1, 2016

(54) UNIVERSAL LAMINOPLASTY IMPLANT

(76) Inventor: Rohit Khanna, Daytona Beach, FL (US)

(*) Notice: Subject to any disclaimer, the term of this patent is extended or adjusted under 35 U.S.C. 154(b) by 0 days.

(21) Appl. No.: 12/661,973

(22) Filed: Mar. 27, 2010

(65) Prior Publication Data

US 2012/0165942 A1 Jun. 28, 2012

Related U.S. Application Data

(63) Continuation-in-part of application No. 10/299,624, filed on Nov. 19, 2002, now Pat. No. 6,660,007, which is a continuation of application No. 10/035,281, filed on Jan. 3, 2002, now abandoned.

(51) Int. Cl.
*A61F 2/44* (2006.01)
*A61B 17/70* (2006.01)
*A61B 17/00* (2006.01)

(52) U.S. Cl.
CPC .. *A61B 17/7071* (2013.01); *A61B 2017/00004* (2013.01)

(58) Field of Classification Search
CPC .................................. A61B 17/7071
USPC .......................... 623/17.11–17.16
See application file for complete search history.

(56) References Cited

U.S. PATENT DOCUMENTS

| | | | |
|---|---|---|---|
| 5,620,448 A | 4/1997 | Puddu | |
| 5,888,223 A | 3/1999 | Bray, Jr. | |
| 5,980,572 A | 11/1999 | Kim et al. | |
| 6,066,175 A | 5/2000 | Henderson et al. | |
| 6,080,157 A * | 6/2000 | Cathro et al. | 606/279 |
| 6,203,548 B1 * | 3/2001 | Helland | 606/105 |
| 6,235,059 B1 | 5/2001 | Benezech et al. | |
| 6,241,771 B1 | 6/2001 | Gresser et al. | |
| 6,544,266 B1 | 4/2003 | Roger et al. | |
| 6,635,087 B2 * | 10/2003 | Angelucci et al. | 623/17.11 |
| 6,660,007 B2 | 12/2003 | Khanna | |
| 6,712,852 B1 | 3/2004 | Chung et al. | |
| 6,997,953 B2 | 2/2006 | Chung et al. | |
| 7,264,620 B2 * | 9/2007 | Taylor | 606/86 A |
| 7,476,238 B2 * | 1/2009 | Panjabi | 606/257 |
| 2002/0095154 A1 * | 7/2002 | Atkinson et al. | 606/61 |
| 2002/0120335 A1 * | 8/2002 | Angelucci et al. | 623/17.16 |
| 2003/0050700 A1 * | 3/2003 | Kihara | 623/17.11 |
| 2003/0125738 A1 * | 7/2003 | Khanna | 606/61 |
| 2003/0125740 A1 * | 7/2003 | Khanna | 606/61 |
| 2004/0030388 A1 * | 2/2004 | Null et al. | 623/17.11 |
| 2004/0064184 A1 * | 4/2004 | Chung et al. | 623/17.11 |
| 2005/0043732 A1 * | 2/2005 | Dalton | 606/61 |
| 2005/0107877 A1 * | 5/2005 | Blain | 623/16.11 |
| 2005/0131412 A1 * | 6/2005 | Olevsky et al. | 606/69 |
| 2005/0251138 A1 * | 11/2005 | Boris et al. | 606/61 |
| 2005/0273100 A1 * | 12/2005 | Taylor | 606/61 |
| 2006/0064091 A1 * | 3/2006 | Ludwig et al. | 606/61 |
| 2008/0009865 A1 * | 1/2008 | Taylor | 606/61 |
| 2008/0215096 A1 * | 9/2008 | Nash et al. | 606/249 |
| 2009/0210012 A1 * | 8/2009 | Null et al. | 606/280 |
| 2010/0057127 A1 * | 3/2010 | McGuire et al. | 606/246 |
| 2010/0063590 A1 * | 3/2010 | Cannestra | 623/17.11 |
| 2010/0069960 A1 * | 3/2010 | Chaput | 606/249 |
| 2010/0185240 A1 * | 7/2010 | Mangione et al. | 606/250 |
| 2010/0241165 A1 * | 9/2010 | Konieczynski et al. | 606/248 |
| 2012/0165942 A1 * | 6/2012 | Khanna | 623/17.16 |

* cited by examiner

*Primary Examiner* — Mary Hoffman

(57) ABSTRACT

The present invention relates various embodiments of a laminoplasty implant comprising a telescopic spacer configured to attach to the vertebra and adjust the space between two cut portions of a vertebra.

20 Claims, 30 Drawing Sheets

UNIVERSAL LAMINOPLASTY IMPLANT

Related U.S. Application Data: Continuation-in-part of application Ser. No. 10/299,624 filed on Nov. 19, 2002 now U.S. Pat. No. 6,660,007, which is a continuation of application Ser. No. 10/035,281 filed on Jan. 3, 2002

BACKGROUND OF THE INVENTION

Cervical stenosis with spinal cord compression and consequent myelopathy is a very common problem encountered by the spine surgeon. The usual cause of multilevel cervical stenosis is spondylosis and/or ossification of the posterior longitudinal ligament. Surgical decompression either through an anterior or posterior approach can be undertaken.

An anterior approach usually involves multilevel corpectomy with fusion and stabilization. The main drawback of this technique is the increased time and complexity of the procedure as well as the risk of pseudoarthrosis and accelerated degeneration at the levels above and below the fusion.

A posterior approach has traditionally involved a simple laminectomy, laminectomy with facet fusion, or laminoplasty. The drawback of a simple laminectomy is the risk of late clinical deterioration from either kyphosis, instability, or post-laminectomy scar formation. Laminectomy with facet fusion decreases the risk of kyphosis but it also decreases the range of motion in the spine and increases the risk of accelerated degeneration at the levels above and below the fusion.

Laminoplasty either through open door or double door technique provides greater stability and range of motion when compared with laminectomy alone. This technique entails laminoplasty for decompression and fixation with a plate with or without laminar fusion. The principle behind laminar fixation is that it maintains the decompression following laminoplasty as well as the displaced lamina in a fixed position thereby also providing stabilization since facet motion is preserved.

U.S. patent application Ser. No. 10/035,281 by the applicant describes several laminar fixation plates with and without a bone spacer that allow for lamina fixation and fusion. U.S. Pat. No. 6,660,007 assigned to the applicant also describes laminoplasty plates for open door and double door techniques with a spacer in the middle to maintain the decompressed lamina position. Different sized spacers are required depending on the extent of the laminar displacement required.

There is a need for a laminoplasty fixation implant that can also be placed through a minimally invasive approach with a variable size adjustable to the spinal anatomy of the patient. The present invention is an apparatus for use in either the open door or double door laminoplasty technique to stabilize the lamina in the spine thereby preserving the range of motion as well as maintaining stability. It also provides for a universal laminoplasty implant with a spacer that can be expanded or reduced in size depending on the patient anatomy and the degree of spinal canal decompression required.

SUMMARY OF THE INVENTION

The present invention relates a laminar fusion and fixation system following either open door or double door laminoplasty technique. This system with the spacer and plate reduces surgical time and simplifies laminar fixation and fusion if needed after laminoplasty.

In one embodiment the lamina fixation device consists of a plate contoured at each end with a hollow telescopic spacer in the middle with adjustable length but uniform width and thickness specific for the cervical, thoracic or lumbar spine. The contoured ends of the plate allows screw placement in the lamina or spinous process on one side and the facet on the other side. The spacer edges can be straight, curved, or contoured with a notch to encase the lamina edge and allow securement to the lamina on one side and the lateral mass or facet on the other side. The hollow spacer can be packed with allograft or autograft bone to provide for lamina fusion. This implant is made of titanium or similar alloy with magnetic resonance imaging compatibility. Alternatively, part of the implant or spacer is solid and made of allograft bone, hydroxyapatite, or similar absorbable fusion material. The spacer can also be made of a radiolucent material like polyaryletherketone or polyetheretherketone (PEEK) which is packed with bone fusion material to allow radiographic assessment of the fusion.

In another embodiment, the hollow spacer contains a compression spring which expands once implanted into the spine thereby pushing the spacer ends to firmly rest and attach to the lamina and facet. This device would be most suitable for a minimally invasive approach undertaken through a small exposure, whereby the implant can be positioned in the spine in a compressed position with a removable instrument and after implantation, the spring distracts the telescopic spacer and fixates the ends against the bones.

In another embodiment, the lamina fixation device is a telescopic spacer construct with extensions on one or both ends designed for lamina fixation following a double door laminoplasty. The spacer in the middle of the plate allows for laminar fusion in the decompressed position once packed with either allograft bone, autograft bone, or bone morphogenic protein and the spacer extensions on both ends securing the device to the lamina on both sides.

In another embodiment, the lamina fixation device telescopic spacer also comprises a compression spring. The longitudinal spacer ends comprise of extensions to secure to the lamina and/or facet edges.

The telescopic spacer allows the extent of the laminar displacement to be adjustable by increasing or decreasing the spacer length after lamina fixation device has been implanted. Henceforth, it avoids the need for different size implants as one implant can be adjusted to fit all variations in spinal anatomy as well as the extent of the spinal canal decompression desired. The spacer telescopic components can also contain an engaging mechanism to interlock with each other through ratchet teeth to maintain the adjusted length. Alternative spacer telescopic engaging mechanisms can include screws, ridges, hooks, recesses, or a ball and socket mechanism.

The procedure as would be undertaken with the use of the laminoplasty fixation system is described as follows. An open door laminoplasty entails creating a gutter at the junction of the lamina and medial aspect of the facet on both sides with the use of a drill. On the side of the laminoplasty opening, the drilling is carried through into the canal or the opening completed with a small kerrison rongeur. At the other side, the inner cortex at the lamina and facet junction is not drilled. The lamina at the open end is elevated and the spinous process pushed away in order to create a greenstick osteotomy and allow for the laminoplasty decompression. Typically, 6-12 millimeters of distraction between the lamina and the facet provides for a good spinal decompression but this can vary dependent on the degree of spinal canal decompression required. In order to maintain the position of the lamina, the pre-contoured laminar fixation implant with the telescopic spacer is positioned between the displaced lamina and the facet. The spacer maintains the displaced position of the lamina and the implant with the contoured ends secures the construct via screws to the lamina and facet. The telescopic spacer length can be adjusted to increase the distance between the lamina and the facet and increase the extent of the spinal canal space if needed.

A trap door or double door laminoplasty is created by drilling on each side at the laminar and lateral mass junction the outer laminar cortex and sparing the inner laminar cortex. The spinous process may also be resected and a midline gutter is also created which extends through the inner cortex which can be opened with a small kerrison rongeur.

The lamina on either side are lifted and opened creating a greenstick osteotomy on each side. In order to maintain the decompressed position of the lamina, a spacer is placed in between the split lamina. The spacer can either be fixated with screws to the lamina or the facets.

A minimally invasive approach is undertaken with small incisions and serial dilation of the soft tissue along with splitting of the paraspinal muscles from the skin to the spine. A tubular port or any other shape retractor is then placed to maintain the exposure. The drilling of the lamina and if needed the spinous process is undertaken with this exposure using either an endoscope or microscope magnification and subsequently the lamina are displaced to widen the spinal canal. A laminoplasty implant is then placed and secured to the lamina and facet. Due to the small exposure, a laminoplasty implant that can contract to allow placement in the spine and then expand to the position desired after implant is ideal for this approach. The telescopic spacers described herein are ideal for this approach. The tubular port is then removed and the skin incision closed. Intra-operative x-rays or a navigation system can be used to localize the spine level and confirm correct implant placement.

Another variation of the open door laminoplasty is the expansive laminoplasty most suited for the thoracolumbar spine. In this method, the lamina on either side at the junction of the facets are drilled and opened. A lateral spinal canal recess decompression and/or foraminotomy is undertaken and the lamina replaced with the spacer construct on both sides between the displaced lamina and facets. The present invention relates a laminar fusion and fixation system following laminoplasty. This system with the telescopic spring spacer reduces surgical time and simplifies laminar fixation after laminoplasty.

The spacer longitudinal ends can be contoured with a notch to allow securement to the lamina on one side and the lateral mass or facet on the other side. The contoured end shape can be curved, straight, or any other shape to encase and secure the lamina or facet edge.

In another embodiment of the bone spacer, the edges have a superior cuff or shoulder that allows securement against the lamina and facet on both sides as well prevent migration of the spacer into the spinal canal.

The spacer can also be resorbable and made of hydroxyapatite or similar absorbable material which is eventually resorbed and/or replaced with autologous bone during the fusion process.

The laminoplasty device can also comprise of a plate made of titanium or similar alloy with magnetic resonance imaging compatibility which is contoured at the edges to allow fixation of the laminoplasty and securement of the spacer. The contoured design of the plate allows screw placement in the lamina or spinous process on one side and the facet on the other side.

In another embodiment the allograft bone or resorbable graft and plate are constructed as a unit with the bone graft/spacer attached to the plate in the middle through either screws or an adhesive material.

In another embodiment, the bone graft and plate are designed for laminar fusion and fixation following double door laminoplasty. The bone graft or spacer in the middle allows for laminar fusion in the decompressed position with the plate design bent on either end securing the spacer to the lamina and facet.

The spacer can be made of any bio-compatible material, including autograft, allograft or xenograft bone, and can be resorbable or non-resorbable in nature. Resorbable materials can include polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are non-reinforced polymers, carbon-reinforced polymer composites, PEEK (polyetheretherketone), and PEAK (polyaryletherketone) composites, shape-memory alloys like nitinol, titanium, titanium alloys, cobalt chrome alloys, stainless steel, ceramics and combinations thereof and others as well.

In another embodiment of the lamina fixation device, the plate has two extensions perpendicular to the longitudinal plate axis that engage the lamina and facet in a fixed position. The perpendicular extensions can be straight, curved, L-shaped, or contoured with a notch to secure the lamina or facet ends. The plate has a telescopic component between the two extensions that allow adjustment of the distance between the extensions to contour to specific spinal anatomical variations. The plate telescopic components interlock with each other through ratchet teeth to maintain the adjusted length. Alternative plate telescopic engaging mechanisms can include screws, ridges, hooks, recesses, and ball and socket mechanism. The plate ends can also be angled up or down if needed to contour to the spinal anatomy and the laminoplasty technique undertaken.

The procedure as would be undertaken with the use of the laminoplasty fixation system is described as follows. An open door laminoplasty entails creating a gutter at the junction of the lamina and medial aspect of the facet on both sides with the use of a drill. On the side of the laminoplasty opening, the drilling is carried through into the canal or the opening completed with a small kerrison rongeur. At the other side, the inner cortex at the lamina and facet junction is not drilled. The lamina at the open end is elevated and the spinous process pushed away in order to create a greenstick osteotomy and allow for the laminoplasty decompression. Typically, about 6-12 millimeters of distraction between the lamina and the facet provides for a good spinal decompression but this can vary depending on the spinal anatomy. In order to maintain the position of the lamina, a pre-designed plate is placed with curved ends to allow one end to secure to the lamina and the other end to the facet with screws. The plate has two extensions perpendicular to the longitudinal plate axis with a telescopic component in between the extensions which can be adjusted to increase the distance between the extensions and therefore, the lamina and the facet and increase the extent of the spinal canal space.

Another variation on the open door laminoplasty is the expansive laminoplasty most suited for the thoracolumbar spine. In this method, the lamina on either side at the junction of the facets are drilled and opened. A lateral spinal canal recess decompression and/or foraminotomy is undertaken and the lamina repositioned with a plate construct on both sides between the facets and lamina.

A trap door or double door laminoplasty is created by drilling on each side at the laminar and lateral mass junction the outer laminar cortex and sparing the inner laminar cortex. The spinous process also be resected and a midline gutter is also created which extends through the inner cortex which can be opened with a small kerrison rongeur. The lamina on either side are lifted and opened creating a greenstick osteotomy on each side. In order to maintain the decompressed position of the lamina, a plate construct is placed with the plate longitudinal ends fixated with screws to the lamina or even the facets. The perpendicular telescopic plate extensions in the middle can be adjusted to maintain the displaced lamina positions.

The telescopic component of the fixation system allows the two portions of the plate to slide into or away from each other thereby adjusting the spacer length and provides for laminar displacement after the device has been implanted. This avoids the need for manually displacing the lamina during surgery at which time with the traditional procedure, several spacer implant sizes are tested to find the right size that conforms to the patient's spine anatomy.

The laminoplasty implants can be made of metal, polymers, ceramics, composites, and/or any bio-compatible material with sufficient strength to maintain the open position of the divided lamina. The implants can be constructed of titanium or titanium alloy for MRI imaging compatibility. It could also be made of a bio-absorbable material (polyesters, poly amino acids, polyanhydrides, polyorthoesters, polyurethanes, polycarbonates, homopolymers, copolymers of poly lactic acid and poly glycolic acid, copolyesters of e-caprolactone, trimethylene carbonate, and para-dioxanone), or allograft or xenograft bone that is absorbed by the body over time once the divided lamina have fused. Alternatively, it could be made of a radiolucent material (polyetheretherketone), plastic, or a combination of plastic and metal to reduce CT and MRI imaging artifact.

The laminoplasty implants can be of a unitary construction, such that the spacer portion, lamina engaging portions and/or the facet engaging portions can be integral or formed from a single piece of material. Alternative embodiments contemplate that the components of the laminoplasty implant can be non-integral, and can be attached to and/or coupled to other components of laminoplasty plate. Embodiments of the laminoplasty implants also describe an expandable spacer portion and/or one or more bendable lamina engagement portions in order to conform to the anatomy of a particular patient. The spacer portions and/or lamina engagement portions can also be pre-bent to accommodate patient anatomy based on anatomical considerations encountered during surgery. The spacer has open ends along the longitudinal plate axis and in other embodiments can also contain open top end to pack the spacer with bone fusion material after implantation and set expansion of the spacer. The bottom end of the spacer is solid and prevents any bone fusion material to migrate into the spinal canal.

Various embodiments and advantages of the current invention are set forth in the following detailed description and claims which will be readily apparent to one skilled in the art.

DETAILED DESCRIPTION OF THE PREFERRED EMBODIMENTS

Figure 1:
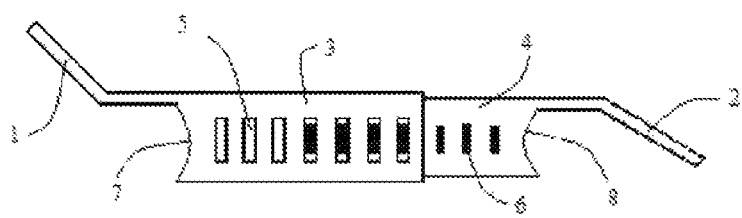
FIG. 1 is a side view of an embodiment of the laminoplasty device.
Figure 2:
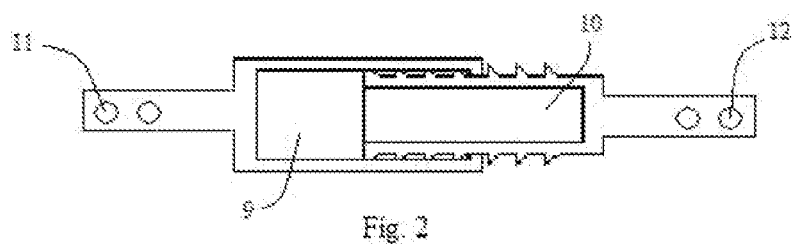
FIG. 2 is a top view of the laminoplasty device.
Figure 3:
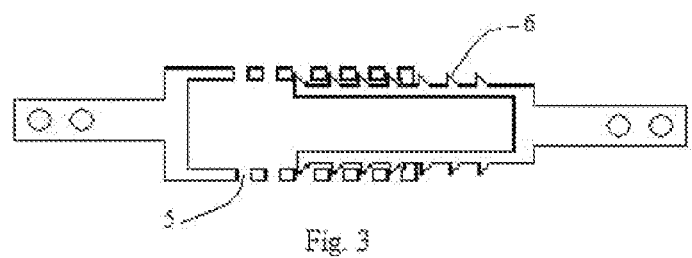
FIG. 3 is a cross-sectional top view of the laminoplasty device.
Figure 4:
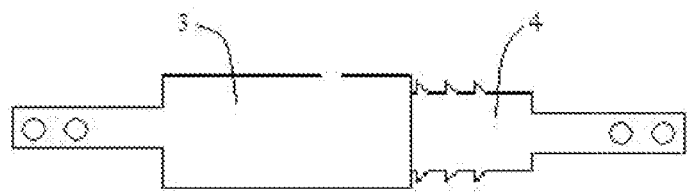
FIG. 4 is a bottom view of the laminoplasty device.
Figure 5:
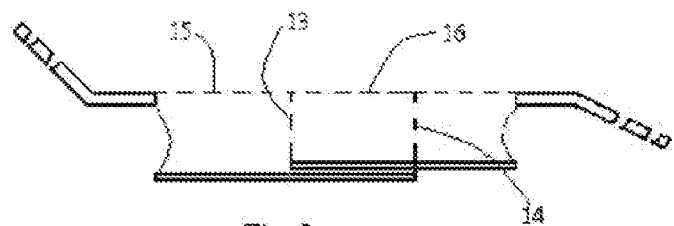
FIG. 5 is a cross-sectional side view of the laminoplasty device.
Figure 6:
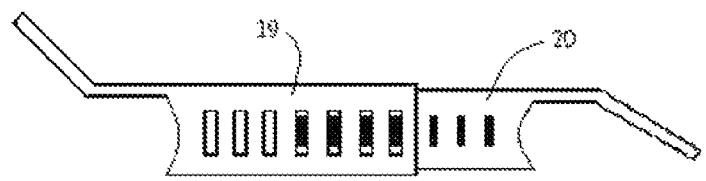
FIG. 6 is a side view of another embodiment of the laminoplasty device.
Figure 7:
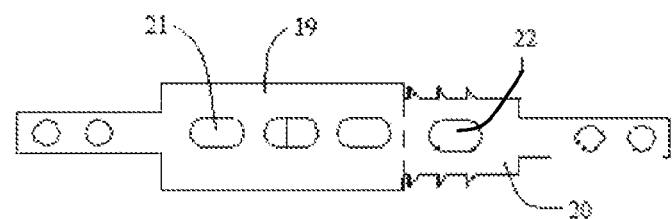
FIG. 7 is a top view of the laminoplasty device.
Figure 8:
FIG. 8 is a cross-sectional top view of the laminoplasty device.
Figure 9:
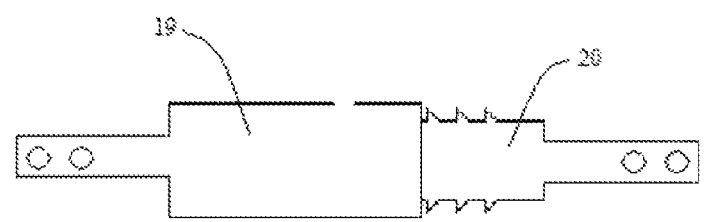
FIG. 9 is a bottom view of the laminoplasty device.
Figure 10:
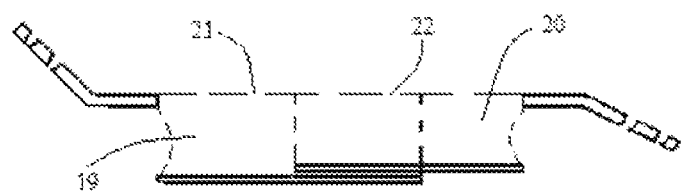
FIG. 10 is a cross-sectional side view of the laminoplasty device.
Figure 11A:
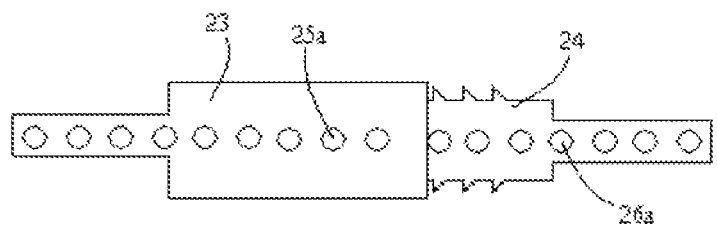
FIG. 11A is a top view of another embodiment of the laminoplasty device.
Figure 11B:
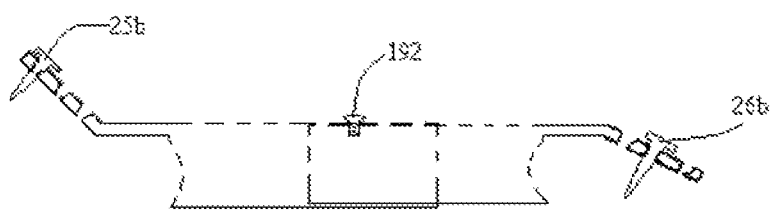
FIG. 11B is a cross-sectional side view of the laminoplasty device.
Figure 11C:
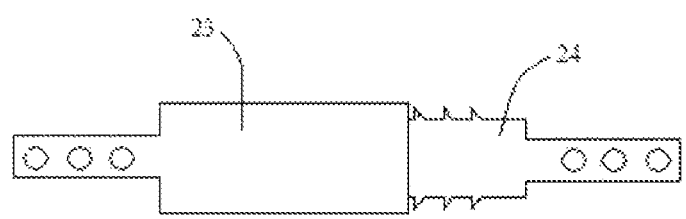
FIG. 11C is a bottom view of the laminoplasty device.
Figure 12:
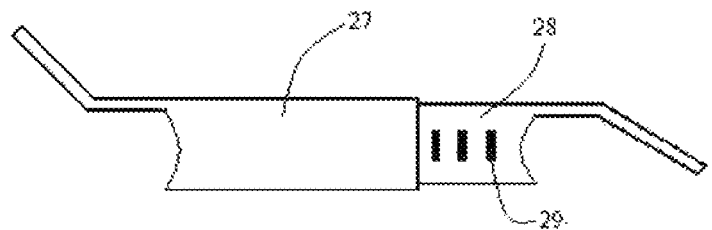
FIG. 12 is a side view of another embodiment of the laminoplasty device.
Figure 13:
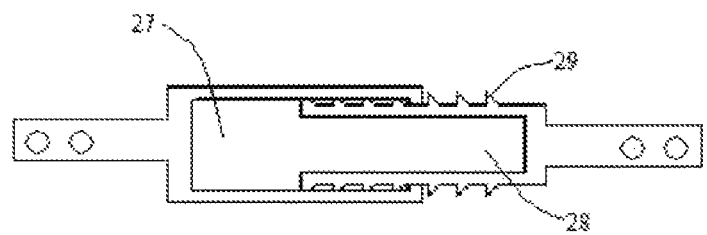
FIG. 13 cross-sectional top view of the laminoplasty device.
Figure 14:
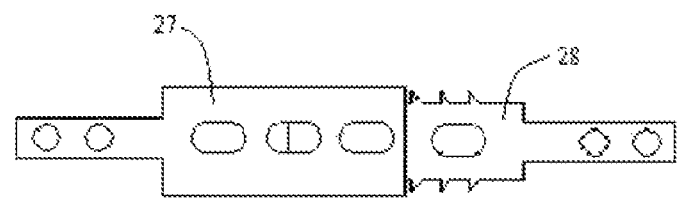
FIG. 14 is a top view of the laminoplasty device.
Figure 15:
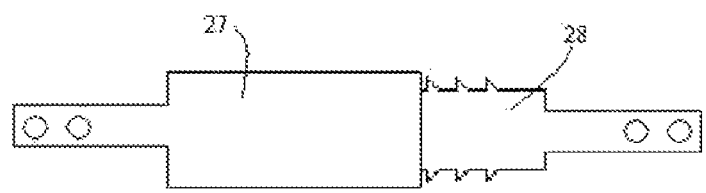
FIG. 15 is a bottom view of the laminoplasty device.
Figure 16:
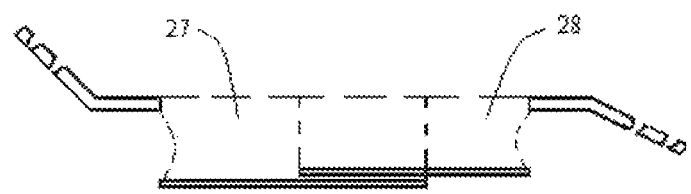
FIG. 16 is a cross-sectional side view of the laminoplasty device.

The present invention describes a device and method for fixation of lamina following a laminoplasty. The laminoplasty device as shown in FIGS. 1-5 comprises a spacer 3 with an extension 1 and a spacer 4 with an extension 2. The spacers 3 and 4 are telescopically engaged to each other with ridges or ratchet teeth 6 on the spacer 4 with the recesses 5 in the spacer 3. The spacers 3 and 4 are hollow with open ends 7 and 8 respectively. The spacer 3 and 4 walls are open at the top 15 and 16 and ends 7, 14 and 8, 13 respectively to allow packing of the hollow spacers after or before implantation with bone fusion material to fuse the lamina with the facet. Bone fusion material can comprise of autograft bone, allograft bone, xenograft bone, demineralized bone matrix, bone morphogenic protein, hydroxyapatite, and other bone fusion extenders. The solid floors 9 and 10 face the spinal canal and prevent the bone fusion material from migrating into the spinal canal. The extension 1 is angled upwards and comprises of holes 11 for placement of a screw into the facet. The extension 2 is angled downwards and comprises of holes 12 for placement of a screw into the lamina. The spacer engaging ends 7 and 8 can be curved, straight, or L-shaped. The telescopically coupled spacers 3 and 4 can be expanded or retracted into each other with a removable instrument depending on the extent of the lamina displacement required after the device is implanted into the spine. In another variation of the above embodiment as shown in FIGS. 6-10, the telescopic hollow spacers 19 and 20 have smaller openings 21 and 22 in the top wall rather than a completely open top wall. In another variation of the above embodiment, as shown in FIGS. 11A-11C, the telescopic spacers 23 and 24 comprises of multiple screw holes 25a and 26a respectively with screw 25b placed into the facet and screw 26b placed into the lamina. Once the desired length of the telescopic spacers is obtained a screw 192 is placed through the overlapping holes 25a and 26a to secure the two spacers in that position. In another variation of the above embodiment as shown in FIGS. 12-16, the telescopic spacers 27 and 28 contain ratchet teeth 29 that engage with each other. The ratchet teeth on the spacer 27 are inside and the ratchet teeth 29 on the spacer 28 are on the outside.

Figure 17:
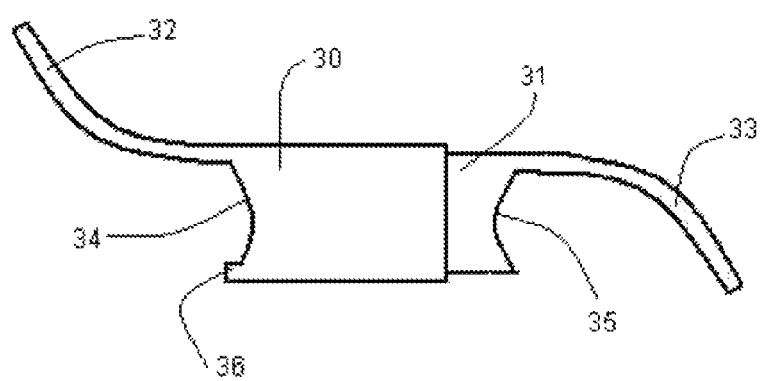
FIG. 17 is a side view of another embodiment of the laminoplasty device in a contracted position.
Figure 18:
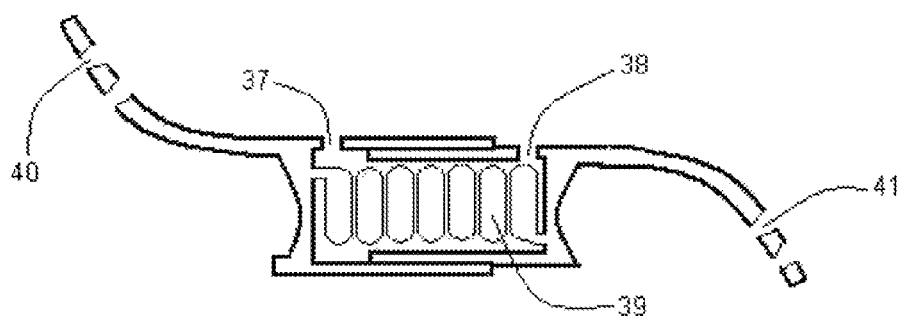
FIG. 18 is a cross-sectional side view of the laminoplasty device in a contracted position.
Figure 19:
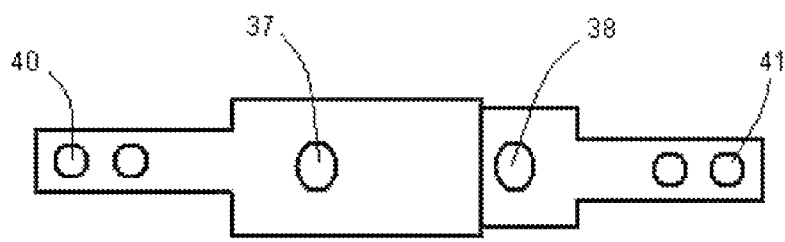
FIG. 19 is a top view of the laminoplasty device in a contracted position.
Figure 20:
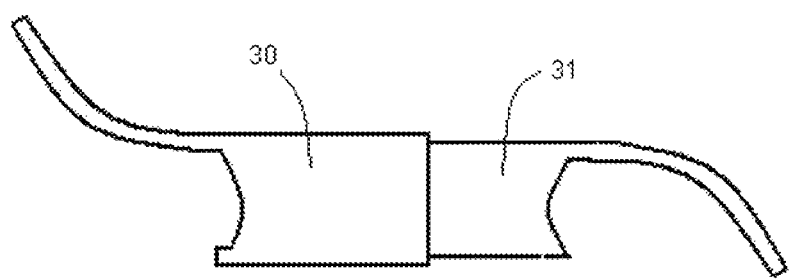
FIG. 20 is a side view of the laminoplasty device in a distracted position.
Figure 21:
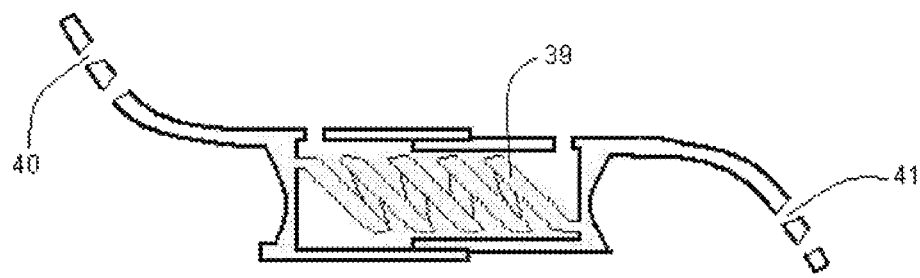
FIG. 21 is a cross-sectional side view of the laminoplasty device in a distracted position.
Figure 22:
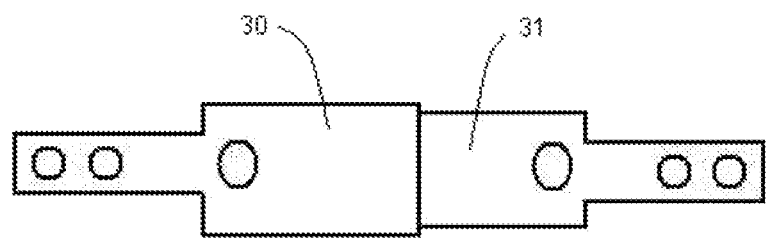
FIG. 22 is a top view of the laminoplasty device in a distracted position.

In another embodiment as shown in FIGS. 17-22, the laminoplasty device comprises a spacer 30 with an extension 32 and a spacer 31 with an extension 33. The spacers 30 and 31 are hollow and telescopically linked to each other. The spacer 30 and 31 ends 34 and 35 are solid and can be curved, straight or L-shaped to engage the facet at the end 34 and the lamina at the end 35. The extension 32 is angled upwards and comprises of holes 40 for placement of a screw into the facet. The extension 33 is angled downwards and comprises of holes 41 for placement of a screw into the lamina. The spacers contain a compression spring 39 that is attached at one side to the spacer 30 end wall 34 and at the other side to the spacer 31 end wall 35. FIGS. 17-19 illustrate the device with the telescopic spacers 30 and 31 in a retracted position with the spring 39 contracted. FIGS. 20-22 illustrate the device telescopic spacers 30 and 31 in an extended position with the spring 39 in a distracted position. The hole 37 in the spacer 30 top wall and the hole 38 in the spacer 31 top wall engage a removable instrument that holds the device in a retracted position and once disengaged after implantation the spacers are distracted by the compression spring 39. The telescopically coupled spacers 30 and 31 are expanded by the spring 39 and engage the lamina at one end and the facet at the other end displacing the lamina.

Figure 23:
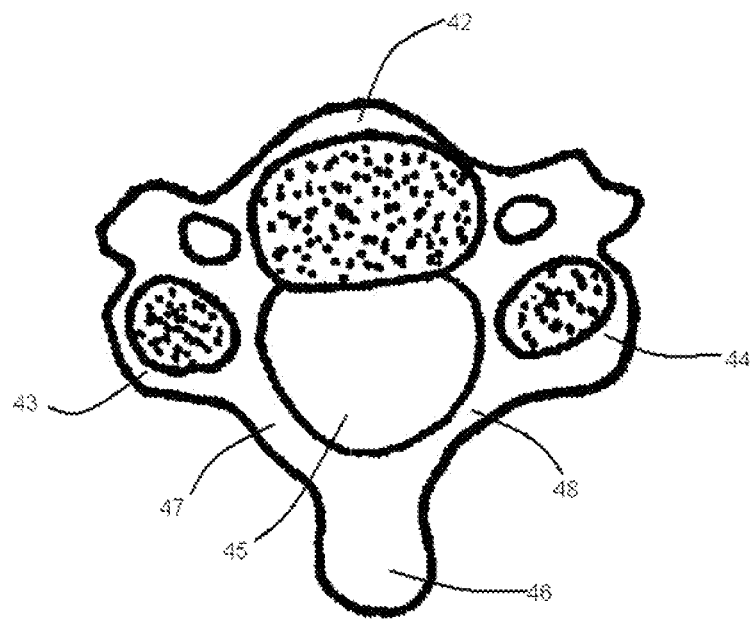
FIG. 23 is a top view of a vertebra.
Figure 24:
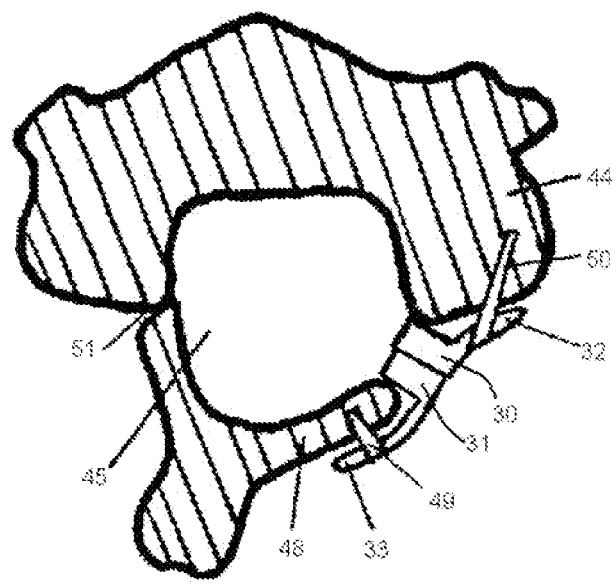
FIG. 24 is a cross-sectional view of a vertebra with a laminoplasty device in place following an open door laminoplasty.

FIGS. 23 and 24 illustrate the method of laminoplasty with the use of the lamina fixation device. As shown in FIG. 23 the spine vertebra comprises of a vertebral body 42, facets 43 and 44, lamina 47 and 48, spinous process 46, and spinal canal 45. FIG. 24 shows the unicortical greenstick osteotomy 51 with the displaced lamina 48 from the facet 44. The device is attached to the severed lamina 48 with a screw 49 and attached to the facet 44 with a screw 50.

Figure 25:
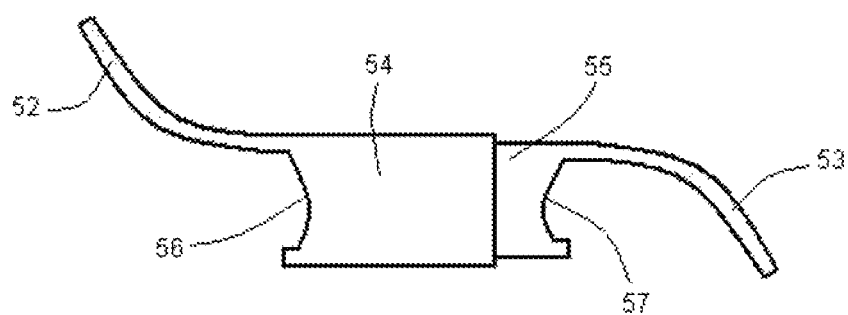
FIG. 25 is a side view of another embodiment of the laminoplasty implant in a contracted position.
Figure 26:
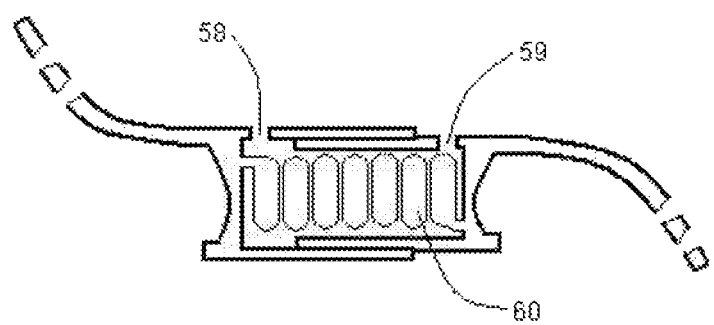
FIG. 26 is a cross-sectional side view of the laminoplasty implant in a contracted position.
Figure 27:
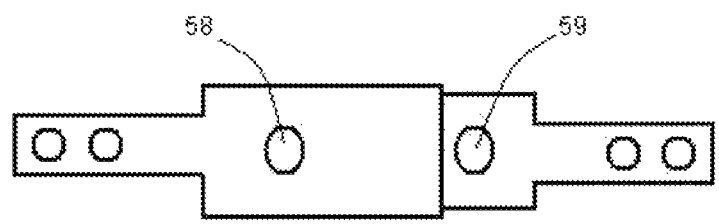
FIG. 27 is a top view of the laminoplasty implant in a contracted position.
Figure 28:
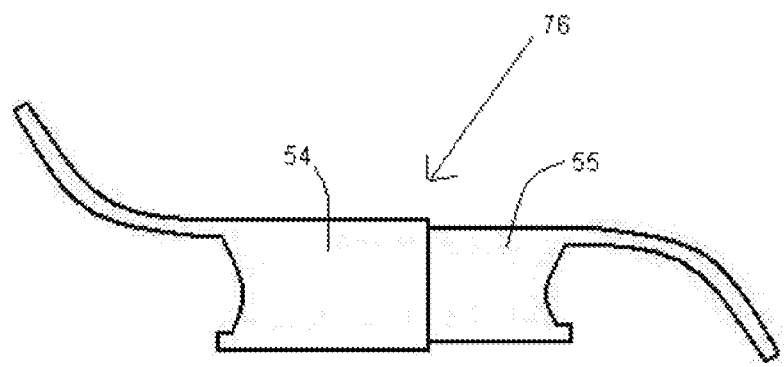
FIG. 28 is a side view of the laminoplasty device in a distracted position.
Figure 29:
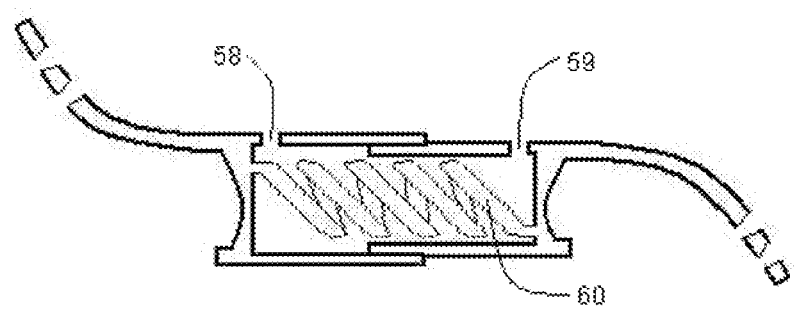
FIG. 29 is a cross-sectional side view of the laminoplasty device in a distracted position.
Figure 30:
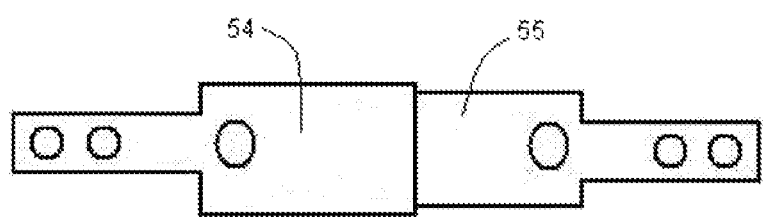
FIG. 30 is a top view of the laminoplasty device in a distracted position.

In another embodiment of the laminoplasty device as shown in FIGS. 25-30, the spacer 54 comprises an extension 52 and a facet engaging end 56. The end 56 has a L-shaped lip to engage the facet. Similarly the spacer 55 has an extension 53 and a lamina engaging end 57 that is L-shaped. The telescopic spacers 54 and 55 also contain a compression spring 60 along with holes 58 and 59 to engage the removable device applicator (not shown). FIGS. 25-27 show the device in a retracted position and FIGS. 28-30 show the device in a distracted position.

Figure 31:
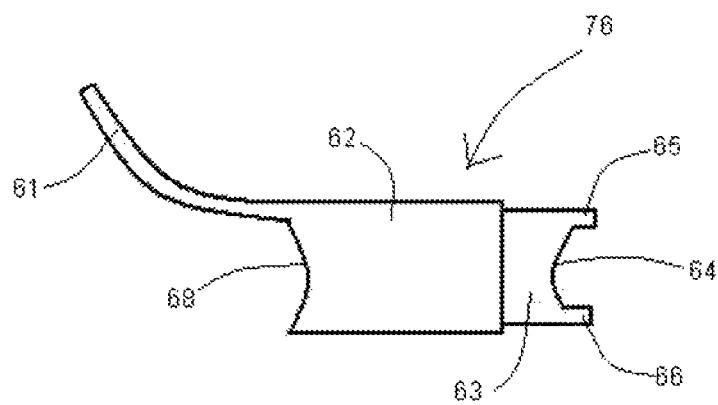
FIG. 31 is a side view of another embodiment of the laminoplasty implant in a contracted position.
Figure 32:
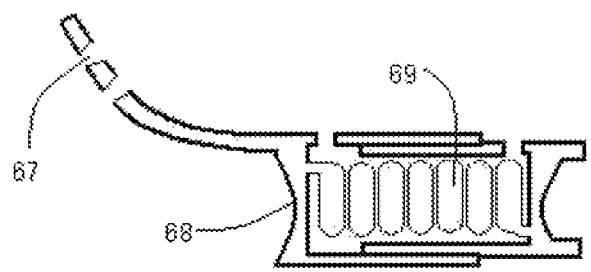
FIG. 32 is a cross-sectional side view of the laminoplasty implant in a contracted position.
Figure 33:
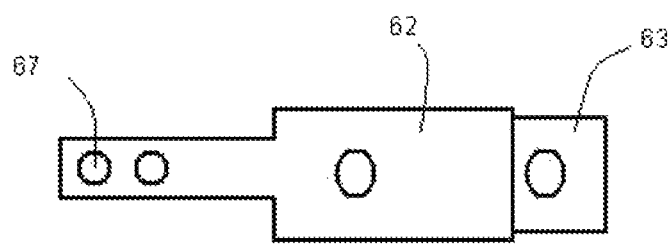
FIG. 33 is a top view of the laminoplasty implant in a contracted position.
Figure 34:
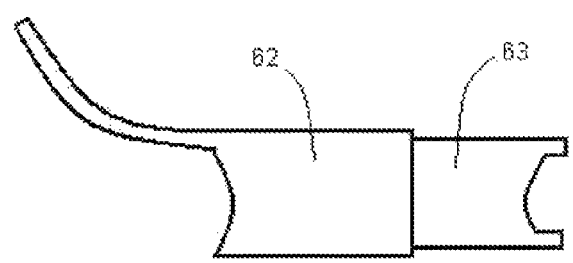
FIG. 34 is a side view of the laminoplasty device in a distracted position.
Figure 35:
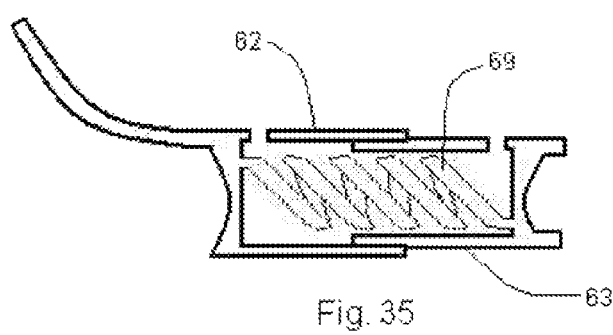
FIG. 35 is a cross-sectional side view of the laminoplasty device in a distracted position.
Figure 36:
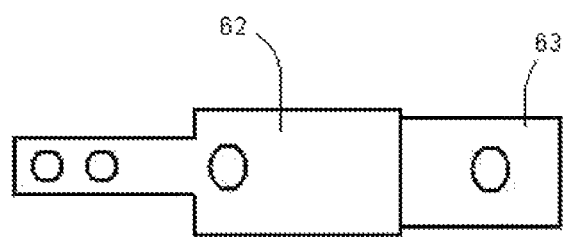
FIG. 36 is a top view of the laminoplasty device in a distracted position.
Figure 37:
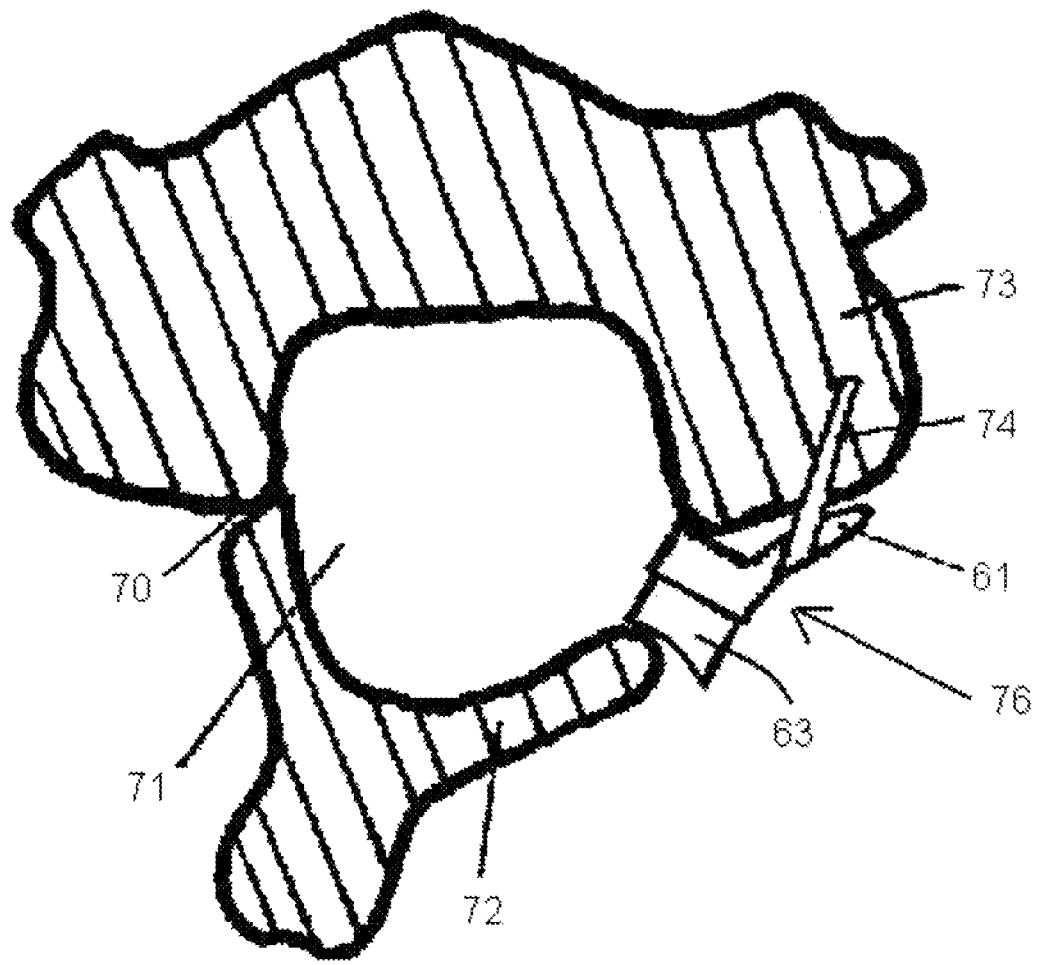
FIG. 37 is a cross-sectional view of a vertebra with a laminoplasty device in place following an open door laminoplasty.
Figure 38:
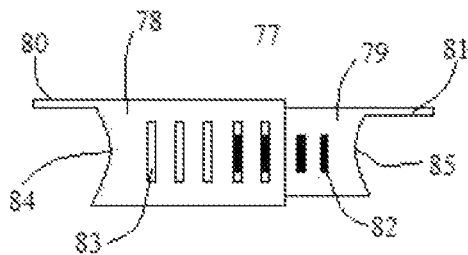
FIG. 38 is a side view of another embodiment of the laminoplasty device
Figure 39:
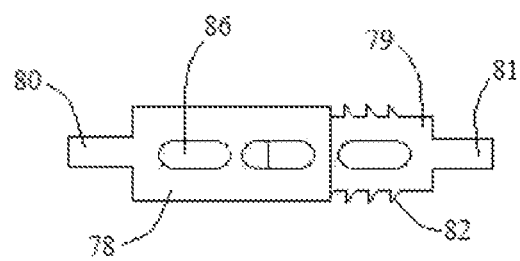
FIG. 39 is a top view of the laminoplasty device
Figure 40:
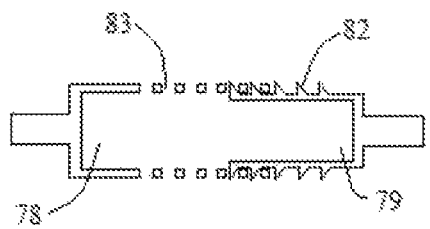
FIG. 40 is a cross-sectional top view of the laminoplasty device.
Figure 41:
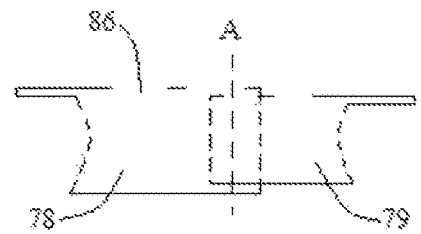
FIG. 41 is a cross-sectional side view of the laminoplasty device.
Figure 42:
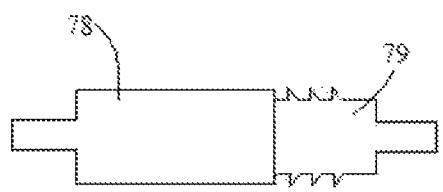
FIG. 42 is a bottom view of the laminoplasty device.
Figure 43:
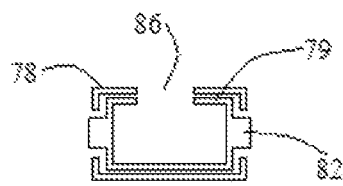
FIG. 43 is a cross-sectional side view of the laminoplasty device taken along line A in FIG. 41.

In another embodiment of the laminoplasty device 76 as shown in FIGS. 31-36, the spacer 62 has a facet engaging end 68 and extension 61 with screw holes 67. The spacer 63 has an end 64 with lamina engaging extensions 65 and 66. The spacers 62 and 63 are telescopically linked by a compression spring 69. FIGS. 31-33 illustrate the device in a retracted position and FIGS. 34-36 illustrate the device in a distracted position. The device 76 illustrated in FIGS. 31-36 is seen implanted in FIG. 37. The lamina greenstick osteotomy 70 allows displacement of the lamina 72 from the facet 73 increasing the spinal canal space 71. The device is placed with the spacer 63 end engaging the lamina 72 and the spacer extension 61 attached to the facet 73 through a screw 74.

The embodiments described in FIGS. 1-37 are designed for use with the open door laminoplasty technique.

Figure 44:
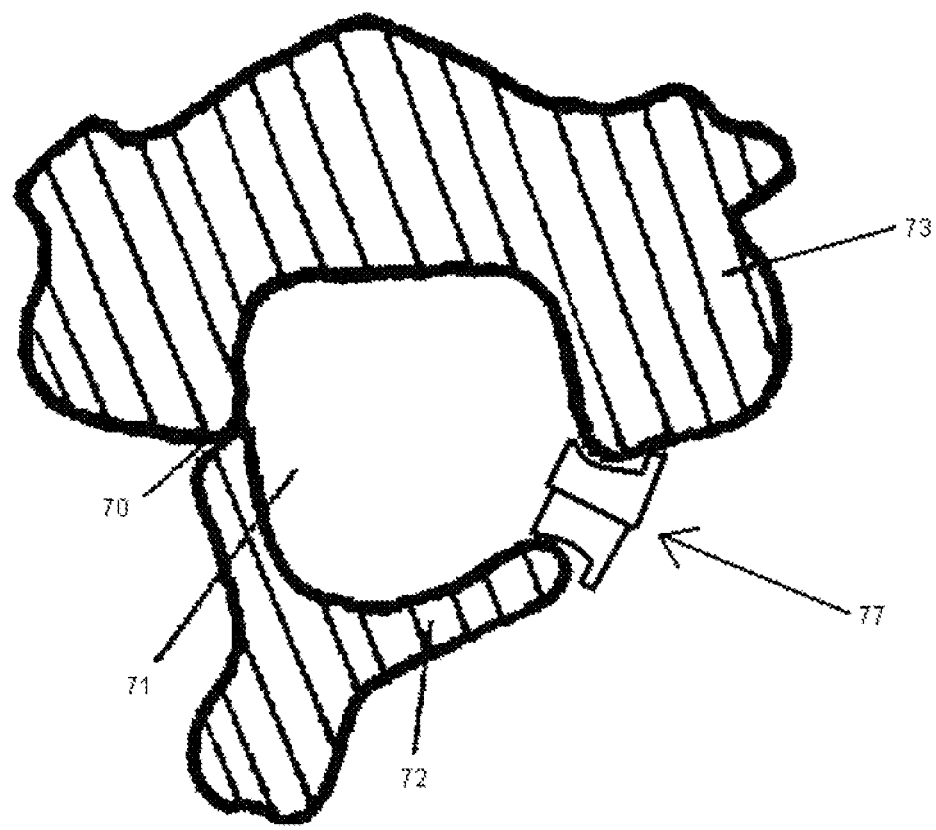
FIG. 44 is a cross-sectional view of a vertebra with a laminoplasty device in place following an open door laminoplasty.
Figure 45:
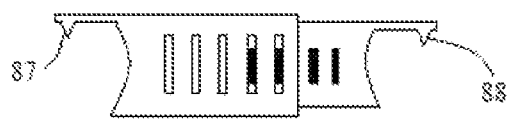
FIG. 45 is a side view of another embodiment of the laminoplasty device.
Figure 46:
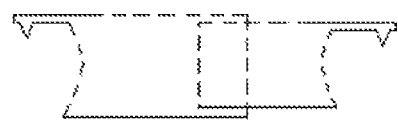
FIG. 46 is a cross-sectional side view of the device.
Figure 47:
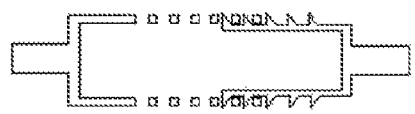
FIG. 47 is a cross-sectional top view of the device.
Figure 48:
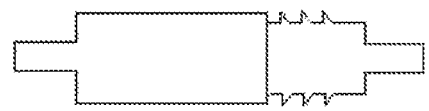
FIG. 48 is a bottom view of the device.
Figure 49:
FIG. 49 is a top view of the device.
Figure 50:
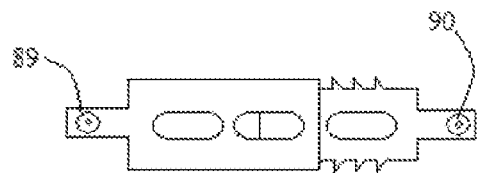
FIG. 50 is a top view of another embodiment of the laminoplasty device.

In another embodiment of the laminoplasty device 77 shown in FIGS. 38-43, the spacer 78 comprises a straight extension 80 and a bone engaging end 84. The spacer 79 has a straight extension 81 and a bone engaging end 85. The spacers 78 and 79 are hollow and telescopically linked with ratchet teeth 82 and recesses 83. The top wall of the spacers also comprises of holes 86 to pack the hollow portions with bone fusion material. The holes 86 can also be used to engage a removable instrument to implant the device in the spine and distract the spacers 78 and 79 if needed. The extensions 80 and 81 prevent the device from migrating into the spinal canal. The device is shown implanted in FIG. 44. The device 77 is seen placed between the split lamina 72 and facet 73. In another variation of the above embodiment as shown in FIGS. 45-49, the telescopic spacer extensions comprise spikes 87 and 88 that engage the bone edges. In another variation of the above embodiment as shown in FIG. 50, the spacers comprise of holes 89 and 90 that engage a screw to fixate the telescopic spacers into the spinal bone.

Figure 51:
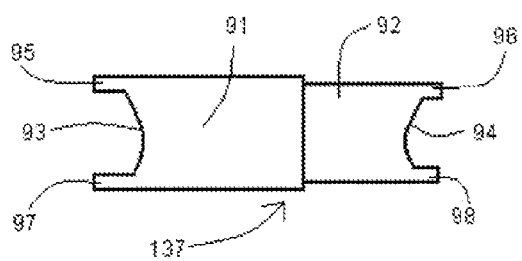
FIG. 51 is a side view of another embodiment of the laminoplasty device in an extended position.
Figure 52:
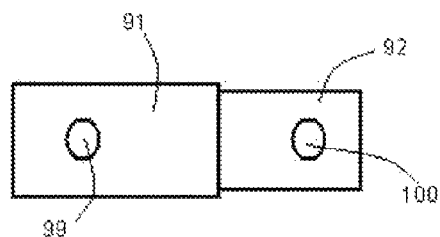
FIG. 52 is a top view of the device in an extended position.
Figure 53:
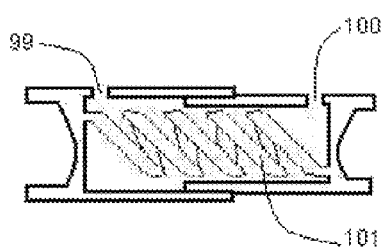
FIG. 53 is a cross-sectional side view of the device in an extended position.
Figure 54:
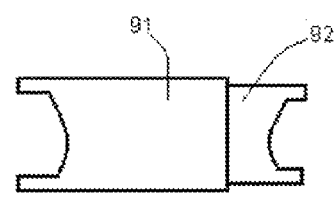
FIG. 54 is a side view of the device in a retracted position.
Figure 55:
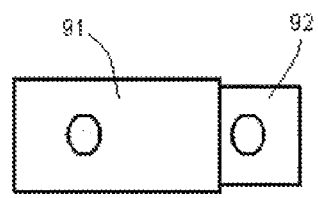
FIG. 55 is a top view of the device in a retracted position.
Figure 56:
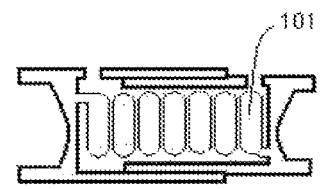
FIG. 56 is a cross-sectional side view of the device in a retracted position.
Figure 57:
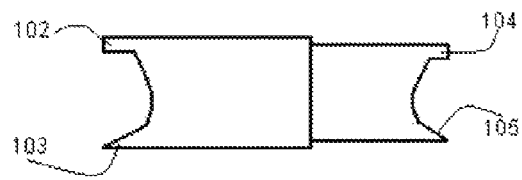
FIG. 57 is a side view of another embodiment of the laminoplasty device in an extended position.
Figure 58:
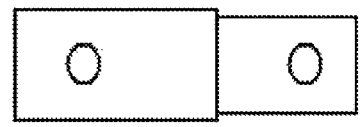
FIG. 58 is a top view of the device in an extended position.
Figure 59:
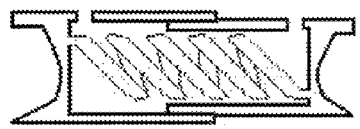
FIG. 59 is a cross-sectional side view of the device in an extended position.
Figure 60:
FIG. 60 is a side view of the device in a retracted position.
Figure 61:
FIG. 61 is a top view of the device in a retracted position.
Figure 62:
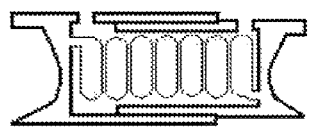
FIG. 62 is a cross-sectional side view of the device in a retracted position.
Figure 63:
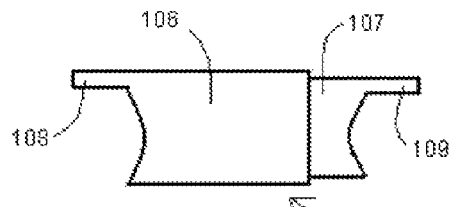
FIG. 63 is a side view of another embodiment of the laminoplasty device in a retracted position.
Figure 64:
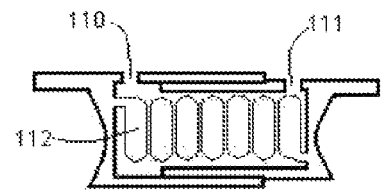
FIG. 64 is a cross-sectional side view of the device in a retracted position.
Figure 65:
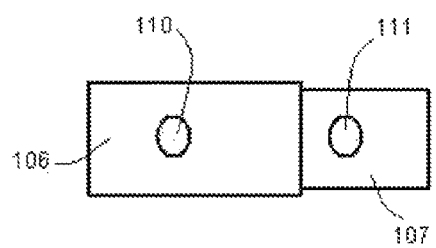
FIG. 65 is a top view of the device in a retracted position.
Figure 66:
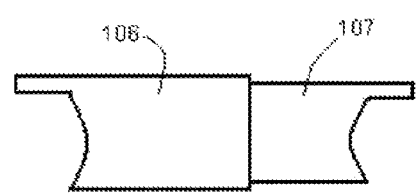
FIG. 66 is a side view of the device in an extended position.
Figure 67:
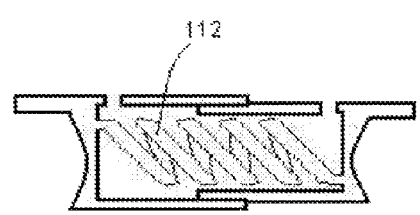
FIG. 67 is a cross-sectional side view of the device in an extended position.
Figure 68:
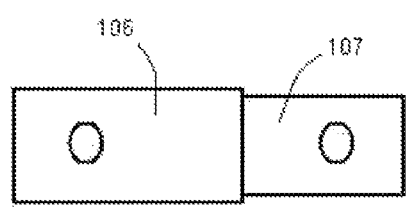
FIG. 68 is a top view of the device in an extended position.
Figure 69:
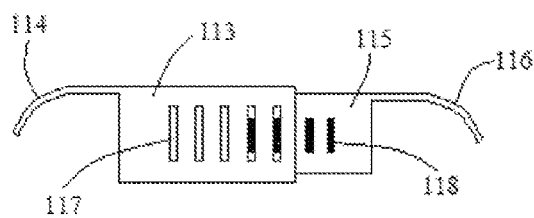
FIG. 69 is a side view of another embodiment of the laminoplasty device.
Figure 70:
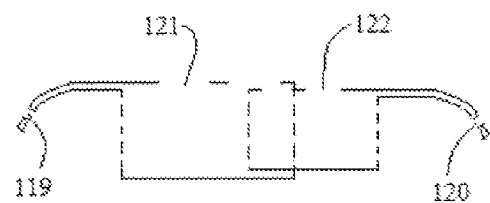
FIG. 70 is a cross-sectional side view of the device.
Figure 71:
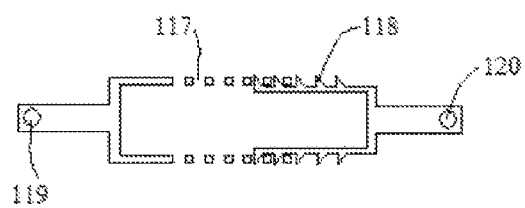
FIG. 71 is a cross-sectional top view of the device.
Figure 72:
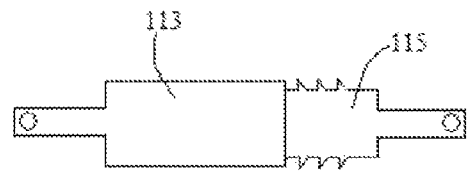
FIG. 72 is a bottom view of the device.
Figure 73:
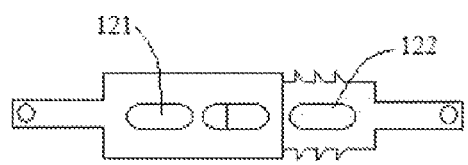
FIG. 73 is a top view of the device.

In another embodiment of the laminoplasty device 137 as shown in FIGS. 51-56, the spacer 91 bone engaging end 93 comprises of extensions 95 and 97. The spacer 92 bone engaging end 94 also comprises of extensions 96 and 98. The spacers 91 and 92 are telescopically linked with a spring 101 and also comprise of holes 99 and 100 to temporarily engage a placement device which maintains the compressed position of the telescopic spacers and once implanted the placement device is disengaged and allows the spring to distract the spacers. The bone engaging end extensions engage with the lamina and/or facet and prevent inward or outward migration of the device. FIGS. 51-53 illustrate the distracted position of the device and FIGS. 54-56 illustrate the contracted position of the device. In a variation of the above embodiment, the bone engaging ends comprise of spikes. As shown in FIGS. 57-62, of the bone engaging extensions 102 and 103 on one side and 104 and 105 on the other side, the lower extensions 103 and 105 comprise of spikes. The spikes 103 and 105 extend into the bone to secure the device whereas the extensions 102 and 105 rest on the bone and prevent inward migration of the device into the spinal canal. FIGS. 57-59 illustrate the distracted position of the device and FIGS. 60-61 illustrate the contracted position of the device. In another variation of the above embodiment, the bone engaging ends comprise of only one extension on each side. As shown in FIGS. 63-68, the spacer 106 comprises a top extension 108 and the spacer 107 comprises an extension 109. The compression spring 112 telescopically links the spacers 106 and 107. The holes 110 and 111 allow for engagement of a placement device. The top extensions 108 and 109 prevent the device from migrating into the spinal canal. FIGS. 63-65 illustrate the contracted position of the device 134 and FIGS. 66-68 illustrate the distracted position of the device.

The embodiments described in FIGS. 38-68 can be used for any of the laminoplasty techniques (open door, double door, or expansive laminoplasty).

Another embodiment of the laminoplasty device for use in the double door laminoplasty technique is shown in FIGS. 69-73. The telescopic spacer 113 is hollow and comprises an extension 114, side wall recesses 117 and top wall holes 121. The telescopic spacer 115 is hollow and comprises an extension 116, side wall ratchet teeth 118 and top wall holes 122. The extensions 114 and 116 are angled downwards and also comprise screw holes 119 and 120 for fixation to the lamina. The spacer 113 and 115 longitudinal ends are open and bone fusion material can be packed inside the hollow spacers.

Figure 74:
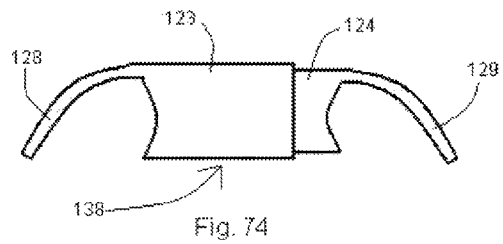
FIG. 74 is a side view of another embodiment of the laminoplasty device in a retracted position.
Figure 75:
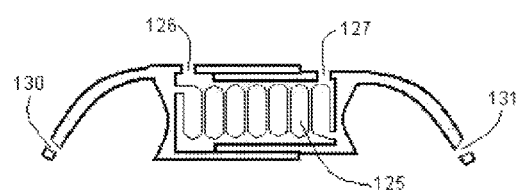
FIG. 75 is a cross-sectional side view of the device in a retracted position.
Figure 76:
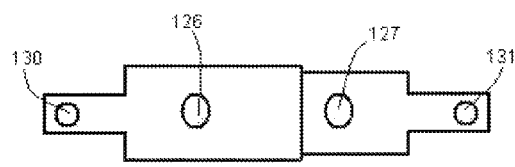
FIG. 76 is a top view of the device in a retracted position.
Figure 77:
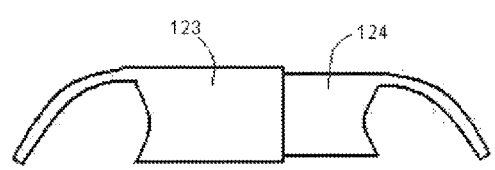
FIG. 77 is a side view of the device in an extended position.
Figure 78:
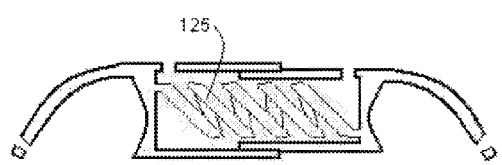
FIG. 78 is a cross-sectional side view of the device in an extended position.
Figure 79:
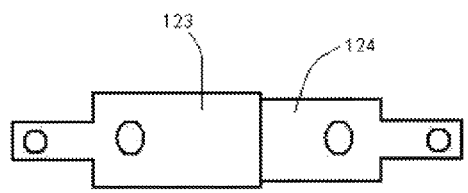
FIG. 79 is a top view of the device in an extended position.

In another embodiment of the laminoplasty device 138 for use in the double door laminoplasty technique as shown in FIGS. 74-79, the spacer 123 comprises an extension 128 angled downwards and the spacer 124 comprises an extension 129 also angled downwards. The spacers 123 and 124 are telescopically linked by a compression spring 125. The spacer 123 comprises of a hole 126 and an extension screw hole 130. The spacer 124 comprises of a hole 127 and an extension screw hole 131. FIGS. 74-76 show the device in a contracted position and FIGS. 77-79 show the device in an extended position.

Figure 80:
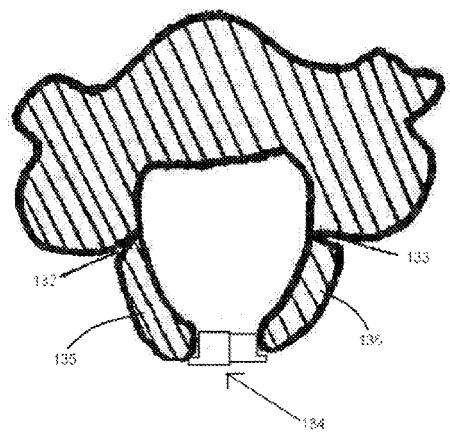
FIG. 80 is a cross-sectional view of a vertebra with a laminoplasty device seen in FIG. 38 or FIG. 63 in place following a double door laminoplasty.
Figure 81:
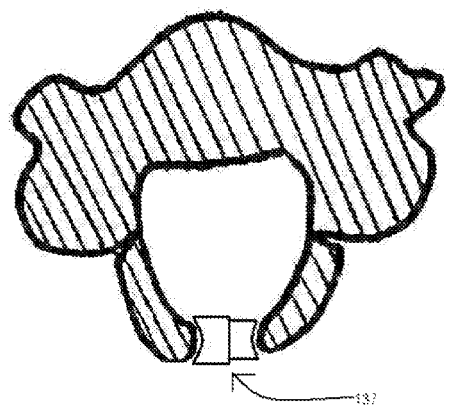
FIG. 81 is a cross-sectional view of a vertebra with a laminoplasty device seen in FIG. 51 in place following a double door laminoplasty.
Figure 82:
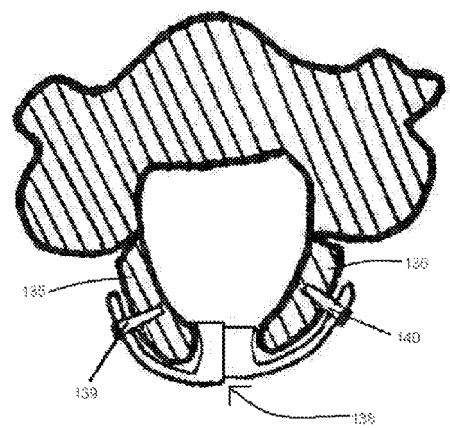
FIG. 82 is a cross-sectional view of a vertebra with a laminoplasty device seen in FIG. 69 or FIG. 74 in place following a double door laminoplasty.
Figure 83:
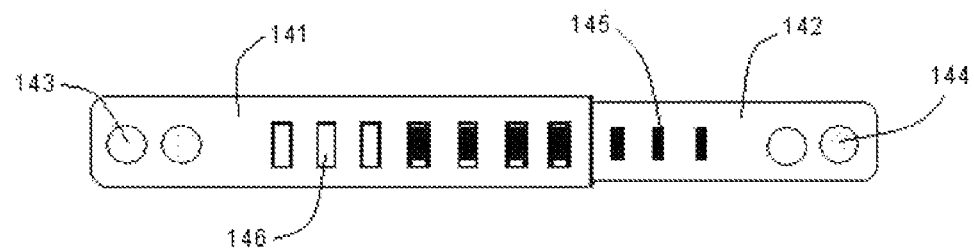
FIG. 83 is a top view of another embodiment of the laminoplasty device.
Figure 84:
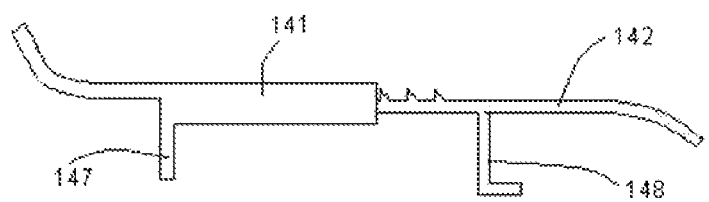
FIG. 84 is a side view of the device.
Figure 85:
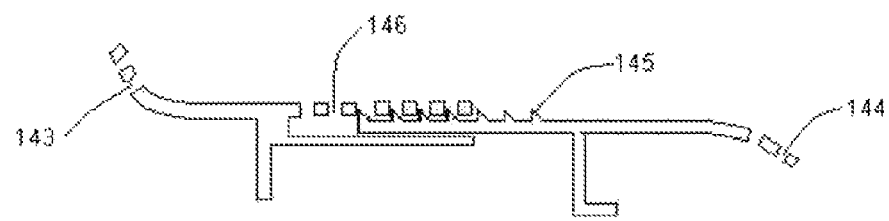
FIG. 85 is a cross-sectional side view of the device.
Figure 86:
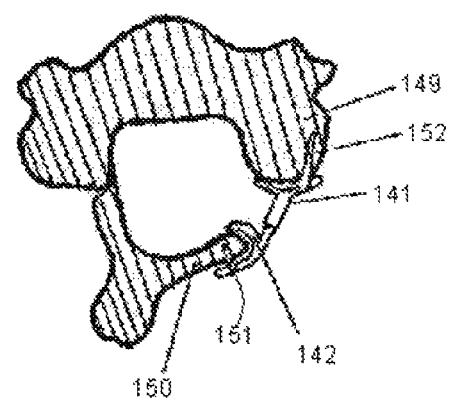
FIG. 86 is a cross-sectional view of a vertebra with the laminoplasty device in place following an open door laminoplasty.

FIG. 80 illustrates the device 134 described in FIGS. 63-68 in place in the spine. With the double door laminoplasty technique, a greenstick osteotomy is created at the junction of the lamina and facet on both sides 132 and 133. The lamina 135 and 136 are also divided in the middle and opened out to increase the spinal canal space. The device 134 is then placed to maintain the opened lamina position as illustrated in FIG. 80. FIG. 81 illustrates the device 137 described in FIGS. 51-56 in place following the double door laminoplasty technique. FIG. 82 illustrates the device 138 described in FIGS. 74-79 in place following a double door laminoplasty. The device 138 is attached to the lamina 135 via screw 139 and the lamina 136 via screw 140.

Figure 87:
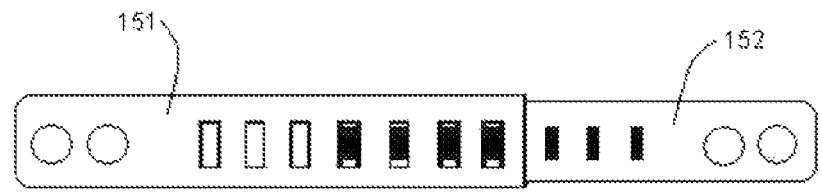
FIG. 87 is a top view of another embodiment of the laminoplasty device.
Figure 88:
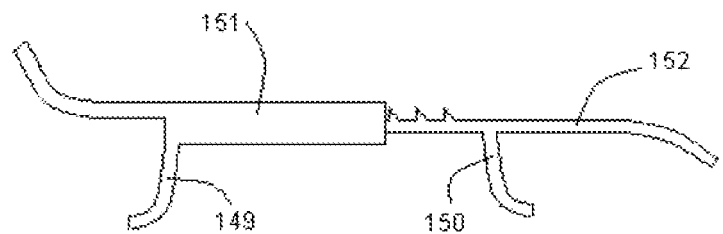
FIG. 88 is a side view of the device.
Figure 89:
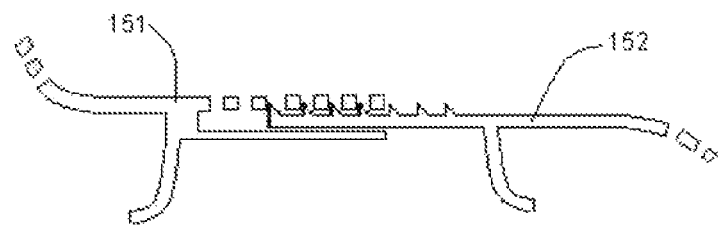
FIG. 89 is a cross-sectional side view of the device.

Another embodiment of the open door laminoplasty device is shown in FIGS. 83-86. The device comprises an elongated telescopic plate 141 with recesses 146 and a perpendicular extension 147. The non-telescopic plate end is angled upwards and comprises of screw holes 143 for attachment to the facet. The device also comprises of another elongated telescopic plate 142 with ratchet teeth 145 and a perpendicular extension 148. The non-telescopic plate end is angled downwards and comprises of screw holes 144 for attachment to the lamina. The telescopic ends of plates 141 and 142 are coupled with each other through ratchet teeth 145 and recesses 146 allowing adjustment of the plate length and distance between the extensions 147 and 148. The extension 147 engages the facet end and the extension 148 engages the lamina end. These perpendicular extensions can be straight, curved, or L-shaped. The device is shown implanted in FIG. 86. The device telescopic plate 141 is attached to the facet 149 via screw 152 and the telescopic plate 142 is attached to the lamina 150 via screw 151. FIGS. 87-89 illustrate another embodiment with the telescopic plate 151 and 152 perpendicular extensions 149 and 150 comprising a curved shape.

Figure 90:
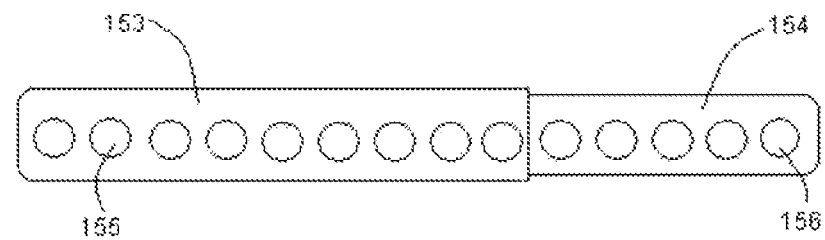
FIG. 90 is a top view of another embodiment of the laminoplasty device.
Figure 91A:
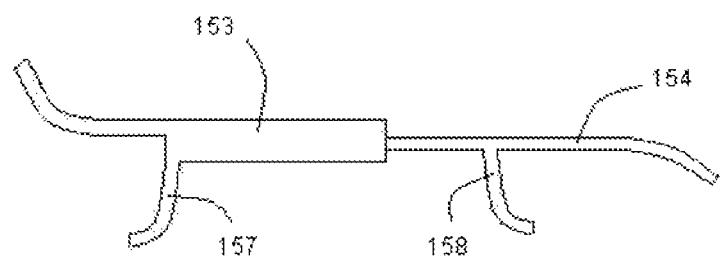
FIG. 91A is a side view of the device.
Figure 91B:
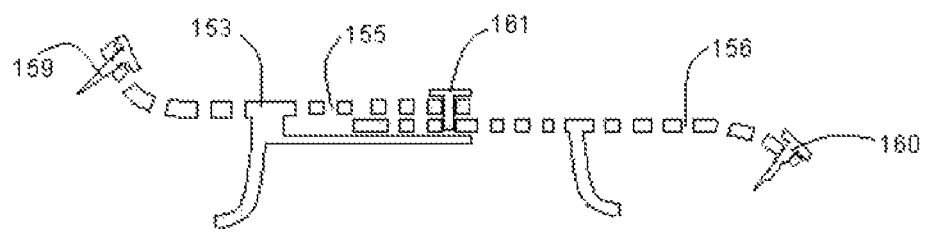
FIG. 91B is a cross-sectional side view of the device.
Figure 92:
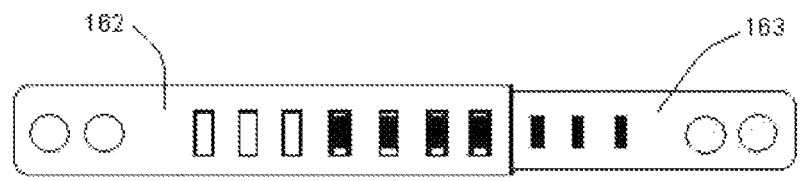
FIG. 92 is a top view of another embodiment of the laminoplasty device.
Figure 93:
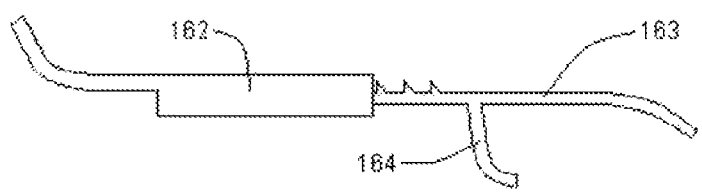
FIG. 93 is a side view of the device.
Figure 94:
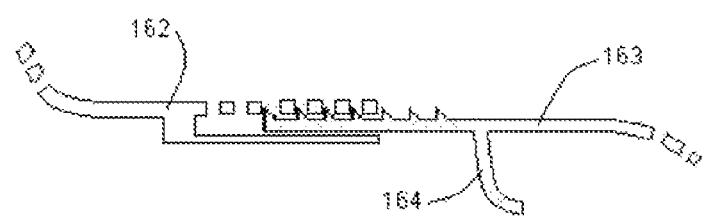
FIG. 94 is a cross-sectional side view of the device.

In another embodiment of the laminoplasty device as shown in FIGS. 90 and 91, the elongated telescopic plates 153 and 154 comprises of multiple holes 155 and 156 and perpendicular extensions 157 and 158. The holes 155 and 156 overlap the telescopic plate components and are fixed in a particular desired distracted or contracted position with a screw 161. The screw 159 at the upward angled plate end attaches to the facet and the screw 160 at downward angled plate end attaches to the lamina.

Figure 95:
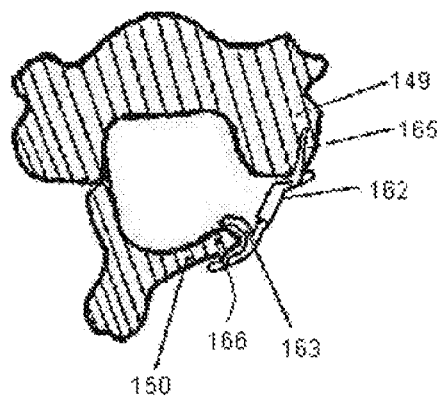
FIG. 95 is a cross-sectional view of a vertebra with the laminoplasty device in place following an open door laminoplasty.
Figure 96:
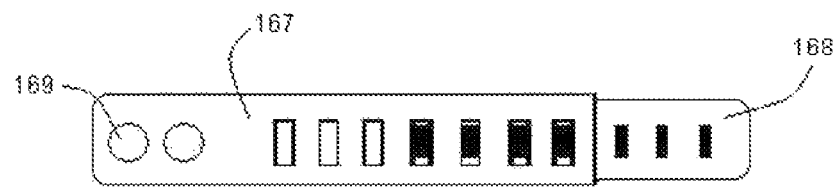
FIG. 96 is a top view of another embodiment of the laminoplasty device.
Figure 97:
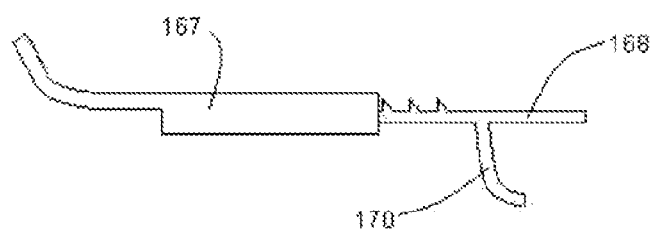
FIG. 97 is a side view of the device.
Figure 98:
FIG. 98 is a cross-sectional side view of the device.

In another embodiment of the laminoplasty device shown in FIGS. 92-95, the plates 162 and 163 are telescopically linked with ratchet teeth. The plate 163 comprises of a perpendicular extension 164 for engagement with the lamina end. FIG. 95 illustrates the device in place with the plate 163 attached to the lamina 150 via screw 166 and the device plate 162 attached to the facet 149 via screw 165.

Figure 99:
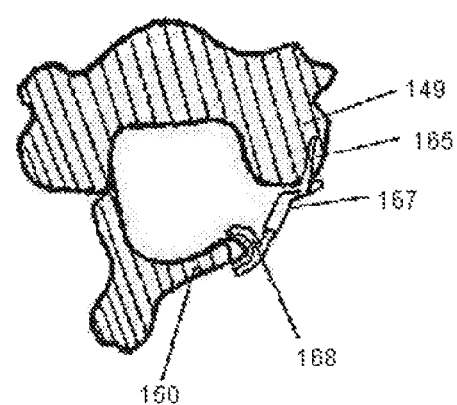
FIG. 99 is a cross-sectional view of a vertebra with the laminoplasty device in place following an open door laminoplasty.
Figure 100:
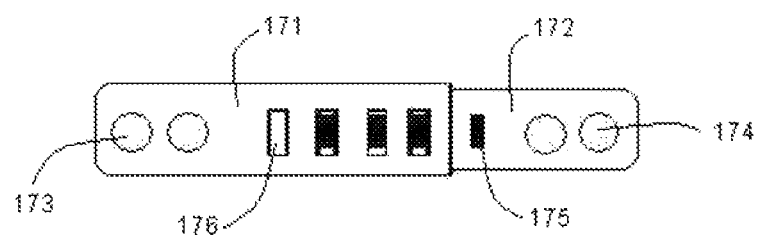
FIG. 100 is a top view of another embodiment of the laminoplasty device.
Figure 101:
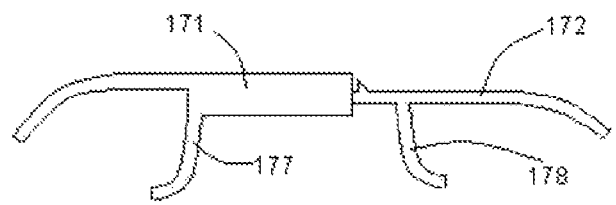
FIG. 101 is a side view of the device.
Figure 102:
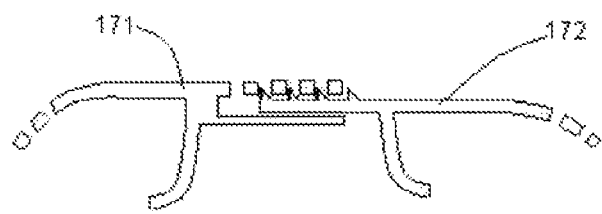
FIG. 102 is a cross-sectional side view of the device.

In another embodiment of the laminoplasty device shown in FIGS. 96-99 the telescopic plate 167 comprises of screw holes 169 for attachment to the facet and the telescopic plate 168 comprises of a perpendicular extension 170 that engages the lamina end. FIG. 99 illustrates the device in place with the plate 167 attached to the facet 149 via screw 165 and the plate 168 secured to the lamina 150 without a screw.

Figure 103:
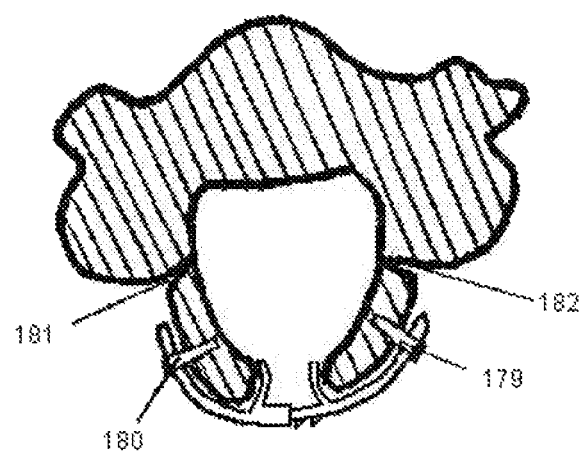
FIG. 103 is a cross-sectional view of a vertebra with the laminoplasty device in place following a double door laminoplasty.
Figure 104:
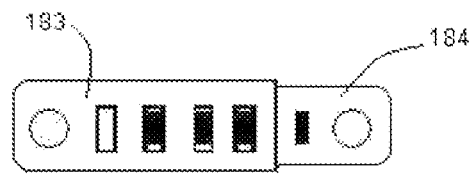
FIG. 104 is a top view of another embodiment of the laminoplasty device.
Figure 105:
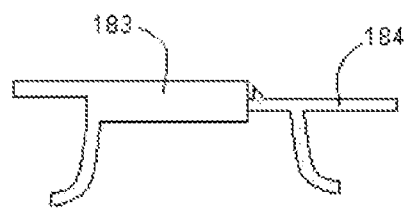
FIG. 105 is a side view of the device.
Figure 106:
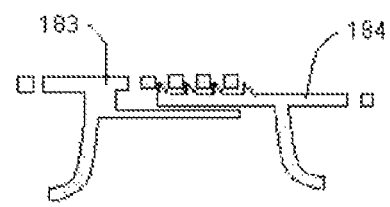
FIG. 106 is a cross-sectional side view of the device.
Figure 107:
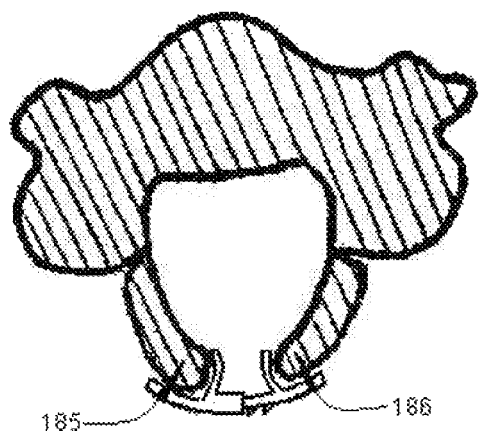
FIG. 107 is a cross-sectional view of a vertebra with the laminoplasty device in place following a double door laminoplasty.
Figure 108:
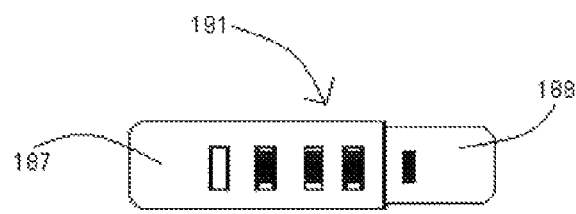
FIG. 108 is a top view of another embodiment of the laminoplasty device.
Figure 109:
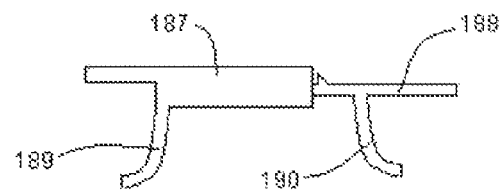
FIG. 109 is a side view of the device.
Figure 110:
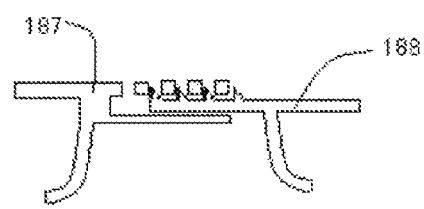
FIG. 110 is a cross-sectional side view of the device.

Another embodiment of the double door laminoplasty device is shown in FIGS. 100-103. The elongated telescopic plate 171 comprises recesses 176 for engagement with the ratchet teeth 175 in the elongated telescopic plate 172. The plate 171 and 172 ends are angled downwards and comprises of screw holes 173 and 174. The plates 171 and 172 also comprise of perpendicular extensions 177 and 178 for attachment to the lamina ends. The telescopic component of the plates allows for adjustment of the distance between the extensions 177 and 178. FIG. 103 illustrates the device in place with the screws 180 and 179 secured to the lamina and greenstick osteotomies on both sides 181 and 182. In another variation of the device described above, the non-telescopic plate ends 183 and 184 are straight rather than angled downwards as shown in FIGS. 104-107. The device is secured to the lamina with screws 185 and 186.

Figure 111:
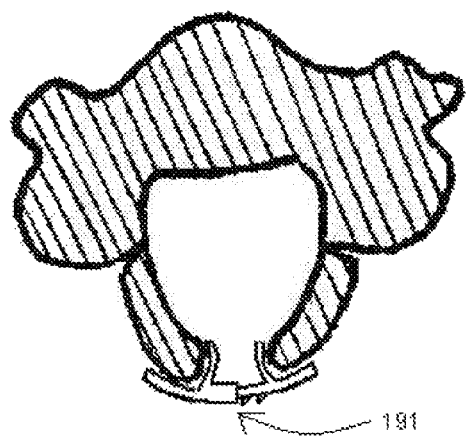
FIG. 111 is a cross-sectional view of a vertebra with the laminoplasty device in place following a double door laminoplasty.
Figure 112:
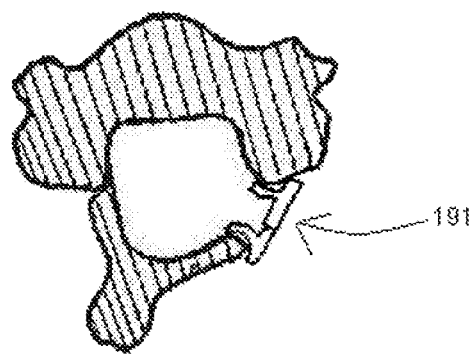
FIG. 112 is a cross-sectional view of a vertebra with the laminoplasty device in place following an open door laminoplasty.

In another embodiment of the laminoplasty device 191, the plate non-telescopic ends are straight rather than being angled downwards. This allows the device to be used for both the open door and the double door laminoplasty techniques. As shown in FIGS. 108-112, the plates 187 and 188 are telescopically linked and comprise of perpendicular extensions 189 and 190 which can be straight, curved or L-shaped. FIG. 111 illustrates the device 191 in place following a double door laminoplasty technique and FIG. 112 illustrates the device 191 in place following an open door laminoplasty technique.

The telescopic component of the device allows the two portions of the plate to slide into or away from each other thereby adjusting the spacer length and provides for laminar displacement after the device has been implanted. This avoids the need for manually displacing the lamina during surgery as well as determining the right spacer size that conforms to the patient's spine anatomy. It provides for a universal laminoplasty implant that can be used in minimally invasive or open laminoplasty techniques. The plate telescopic components interlock with each other through ratchet teeth to maintain the adjusted length. Alternative plate telescopic engaging mechanisms can include screws, ridges, hooks, recesses, ball and socket mechanism among other variations.

While the inventions described here are specific, any variations to the described embodiments falls within the scope of the current invention and the protection granted therein.

What is claimed is:

1. A method comprising:
performing a laminoplasty procedure;
providing a bone fixation device; wherein the bone fixation device comprises at least one longitudinal plate with a proximal end and a distal end, the plate is adapted to be configured so that at least one end engages a portion of a lamina, the plate including a hollow rectangular portion with a partially hollow top wall, a solid bottom wall, lamina engaging hollow end walls, at least one side wall having recesses, and a spacer portion having side wall teeth, wherein the hollow rectangular portion and the spacer portion are telescopically engaged to each other with the side wall recesses and the side wall teeth; the hollow rectangular portion is moveable between a retracted position and an extended position to accommodate a length of a lamina displacement.

2. The method of claim 1, further comprising: a plurality of hollow engaging portions, which includes overlapped slidably engaging portions allowing the least one longitudinal plate to move between the retracted and extended positions.

3. The method of claim 1, wherein the plate further including plurality of apertures adapted to receive fasteners to fasten at least a portion of the plate to at least a portion of the lamina.

4. The method of claim 2, wherein the plurality of hollow engaging portions is adapted to receive bone fusion materials, which includes autograft bone, allograft bone, xenograft bone, bone morphogenic protein, and hydroxypatic.

5. The method of claim 1 wherein the plate further including an engaging mechanism to stabilize the plate after implementation.

6. The method of claim 1 wherein the distal end and the proximal end of the plate are configured to engage a portion of the lamina.

7. The method of claim 1 wherein the top wall is configured to receive bone fusion materials.

8. The method of claim 1 wherein each of the proximal and distal ends of the plate are contoured to engage a portion of the lamina to hold and stabilize the lamina.

9. The method of claim 1 wherein the plate includes at least one adjustable energy storing mechanism to enable the device to move between the retracted and extended positions and stabilize the device after implantation.

10. The method of claim 1 wherein each proximal and distal ends further include at least one extension attachable to a portion of the lamina.

11. The method of claim 10 wherein each end is configured to receive at least one fastener to fasten the end to a portion of the lamina.

12. The method of claim 10 wherein the extension is arcuately extending to attach to a portion of the lamina.

13. A method comprising:
performing a laminoplasty procedure;
providing a bone fixation device; wherein the bone fixation device comprises at least one longitudinal plate with a proximal end and a distal end, the at least one longitudinal plate is adapted so that each of the proximal end and the distal end engages a portion of a lamina, the at least one longitudinal plate includes a couple of slidably engaging portions allowing the at least one longitudinal plate to move between a retracted position and an extended positions to accommodate the length of the displaced lamina, and wherein one of the engaging portions is a hollow rectangular portion, is adapted to receive bone fusion materials, and includes a hollow end wall for engaging the lamina and one side wall having recesses, and wherein the other engaging portion includes a hollow end wall for engaging the lamina and a side wall with teeth for telescopic engagement with the side wall recesses, and wherein the at least one longitudinal plate is configured to attach to any portions of a lamina along the longitudinal axis of the at least one longitudinal plate.

14. The method of claim 13 wherein the plate further includes plurality of apertures adapted to receive fasteners to fasten portion of the plate to portions of the lamina.

15. The method of claim 13 wherein the bone fusion material includes autograft bone, allograft bone, xenograft bone, bone morphogenic protein, and hydroxypatic.

16. The method of claim 13 wherein the plate further includes an engaging mechanism to stabilize the plate after implementation.

17. The method of claim 13 wherein the distal end and the proximal end of the plate are adapted to engage a portion of the lamina.

18. The method of claim 13 wherein the top wall is configured to receive bone fusion material.

19. The method of claim 13 wherein each of the proximal end and the distal ends is contoured to engage a portion of the lamina to hold and stabilize the lamina.

20. The method of claim 13 wherein the couple of slidably engaging portions are telescopically coupled to allow expansion and retraction.

* * * * *